United States Patent [19]

Moore

[11] 4,143,079

[45] Mar. 6, 1979

[54] NOVEL PROCESS FOR PRODUCTION OF PERFLUORO P-METHANE FROM PINENE

[75] Inventor: Robert E. Moore, Wilmington, Del.

[73] Assignee: Suntech, Inc., Philadelphia, Pa.

[21] Appl. No.: 905,693

[22] Filed: May 15, 1978

[51] Int. Cl.² ............................................. C07C 17/00
[52] U.S. Cl. ................................................. 260/648 F
[58] Field of Search ..................................... 260/648 F

[56] References Cited

U.S. PATENT DOCUMENTS 2,487,820  11/1949  McBee et al. ..................... 260/648 F
2,631,170  3/1953   Fowler .............................. 260/648 F
4,041,086  8/1977   Moore et al. ..................... 260/648 F Primary Examiner—Delbert E. Gantz
Assistant Examiner—Joseph A. Boska
Attorney, Agent, or Firm—J. Edward Hess; Donald R. Johnson; Stanford M. Back

[57] ABSTRACT

Pinene can be converted to perfluoro-p-menthane in high yield by first hydrogenating pinene to form pinane, and then perfluorinating the same with $CoF_3$. Ring cleavage of the pinane to form p-menthane is achieved simultaneously with the perfluorination in a single step to obtain perfluoro-p-menthane, a valuable synthetic blood substitute material.

3 Claims, No Drawings

NOVEL PROCESS FOR PRODUCTION OF PERFLUORO P-METHANE FROM PINENE

CROSS-REFERENCE TO RELATED CASES

This application relates to an improved process for making a synthetic blood substitute disclosed in copending application Ser. No. 921,428, filed in the name of Moore and Clark on July 3, 1978.

BACKGROUND OF THE INVENTION

This invention relates to a process for preparing perfluoro-p-menthane. More particularly, this invention relates to a process for converting pinene or pinane to perfluoro-p-menthane in high yield.

Conventionally, perfluoro-p-menthane is prepared by perfluorinating-p-menthane (1-methyl-4-isopropylcyclohexane) which in turn is obtained by hydrogenating p-cymene. However, alternate sources of this material, using other available starting materials, would be highly desirable.

SUMMARY OF THE INVENTION

In accordance with the present process, it has now been found that pinane can be converted to perfluoro-p-menthane in a single step, and in high yield, in accordance with the following reaction scheme:

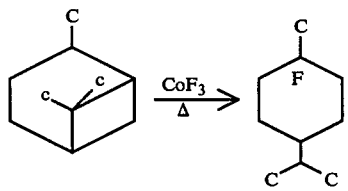

in which "F" designates perfluorination.

DESCRIPTION OF THE INVENTION

The preparation of perfluoro-p-menthane desirably proceeds from pinane. Alternatively, it will be evident that this material may, in turn, be obtained by first hydrogenating pinene, a commercially available material, in a manner shown in Example 1 below.

In the ring cleavage-perfluorination of pinane, the reaction is desirable carried out in a horizontal, four-zone reactor fitted with paddles for stirring a bed of $CoF_3$ at temperatures and for time periods described below.

FLUORINATION REACTOR DESCRIPTION

In the following examples, the pinane compound is charged into a preheater by means of a Howard infusion syringe pump. The preheater is maintained at a temperature sufficiently high to vaporize this compound prior to entering the reactor. The reactor itself is a horizontal 3.5' × 3" I.D. monel tube containing 3500 g $CoF_3$ which is stirred by a series of paddles connected to a central shaft. The reactor is divided into 4 separate heating zones to allow it to be thermally graduated.

Preferably, the material is passed through the reactor two times. The first pass is made with the reactor temperatures somewhat above the estimated boiling points of the materials being charged. As fluorination takes place, the boiling point of the product increases until 50% of the hydrogens have been replaced. Further fluorination causes a decrease in the boiling point of the product. The first pass is generally made at a moderate charge rate, desirably at a rate of 0.123–0.247 cc/min, with the reactor thermally graduated from just above the boiling point of the pinane charge material i.e., 175° C., to approximately 50° C. above its boiling point. The second pass is made at considerably higher temperatures (approximately 100° C. greater across the reactor) to complete the perfluorination.

The product is removed from the reactor through traced lines into a series of traps varying in temperature from 0° C. to −78° C. which are designed not only to remove product but also HF and other gaseous products. A 3 to 4 hour nitrogen purge is required to remove all product from the reactor.

After the reactor has been purged sufficiently with nitrogen to remove the products of fluorination, the reactor temperature is adjusted to 250° C. in all 4 zones. The shaft is rotated at 5–7 rpm. The valving system is then changed to open the fluorine line into the reactor. The rate of fluorine addition is monitored by the fluorine regulator and flowmeter. The reaction of fluorine with $CoF_3$ is essentially quantitative and highly exothermic. The course of the regeneration is easily followed by observing the progression of the exotherm from Zone 1 to Zone 4 of the reactor.

EXAMPLE 1

Commercially avaiable pinene (Eastman Practical Grade) was distilled through a twelve inch Vigreux column. From a one-liter change, the first 200 ml were discarded, then 600 ml of material boiling at 154° C. were collected. 150 ml of this center cut were placed in a high pressure steel reactor with 2 grams 5% palladium on carbon catalyst. The reactor was pressured to 2000 psig with hydrogen intermittently being added as necessary. The reaction was complete before 200° C. was reached, but the mixture was shaken at 200° C. for 6 hours for added certainty. The clear colorless product, pinane, was recovered by filtering the catalyst from the mixture.

EXAMPLE 2

Hydrogenated pinene (27.2g) was pumped at 0.123 cc/min through the aforedescribed horizontal $CoF_3$ bed which was thermally graded from 175° to 250° C. between the inlet and the outlet respectively. The dried product was passed through the reactor at 0.382 cc/min. for a second time at a temperature varying from 285° to 360° C. The crude product weighed 79.3g. Gas chromatographic analysis, IR, mass spec, and 19 FNMR showed the produce to be perfluoro-1-methyl-4-isopropylcyclohexane (perfluoro-p-menthane). This product was identical in all respects to the product obtained from the fluorination of p-cymene.

The invention claimed is:

1. A process for the preparation of perfluoro-1-methyl-4-isopropylcyclohexane which comprises perfluorinating pinane by contacting it with $CoF_3$ at a temperature greater than 175° C.

2. The process of claim 1 wherein the reaction is carried out in a multi-zone reactor in which the temperature is graduated from zone to zone across the reactor with the highest temperature at the outlet of said reactor.

3. The process of claim 1 wherein the pinane product is recycled through the reactor a second time at an overall temperature about 100° C. higher than that of the first pass.

* * * * *